US00PP21094P2

(12) United States Plant Patent
Giesen

(10) Patent No.: US PP21,094 P2
(45) Date of Patent: Jun. 22, 2010

(54) *NEMESIA* PLANT NAMED 'CNEM PINKA'

(50) Latin Name: *Nemesia fruticosa*
Varietal Denomination: Cnem Pinka

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 8 days.

(21) Appl. No.: 12/291,204

(22) Filed: Nov. 7, 2008

(51) Int. Cl.
*A01H 5/00* (2006.01)

(52) U.S. Cl. ..... Plt./458
(58) Field of Classification Search ..... Plt./458
See application file for complete search history.

*Primary Examiner*—Annette H Para
*Assistant Examiner*—Louanne C Krawczewicz Myers
(74) *Attorney, Agent, or Firm*—S. Matthew Edwards

(57) ABSTRACT

A new *Nemesia* plant named 'Cnem Pinka', particularly distinguished by the purple/pink flowers, a relatively compact growth habit that is semi-spreading and mounding, strong stems, full well branched plant with medium-green foliage and relatively large rounded leaves, good floriferiousness, and a slightly sweet fragrance.

1 Drawing Sheet

Latin name of the genus and species of the plant claimed: *Nemesia fruticosa, syn. N fruticans.*

Varietal denomination: 'Cnem Pinka'.

BACKGROUND OF THE NEW PLANT

The present invention comprises a new *Nemesia*, botanically known as *Nemesia fruticosa* and hereinafter referred to by the variety name 'Cnem Pinka'.

'Cnem Pinka' is a product of a planned breeding program. The new cultivar 'Cnem Pinka' has purple/pink flowers, a relatively compact growth habit that is semi-spreading and mounded, strong stems, full well branched plant with medium-green foliage and relatively large rounded leaves, good floriferiousness, and a slightly sweet fragrance.

'Cnem Pinka' originated from a hybridization in a controlled breeding program in Andijk, Netherlands. The female parent was an unpatented hybrid seedling identified as 'NE04-57-1' with white color. 'NE04-57-1' has larger foliage, thinner stems, and smaller petals than 'Cnem Pinka'.

The male parent of 'Cnem Pinka' was an unpatented hybrid seedling identified as 'NE05-14-2' with white color. 'NE05-14-2' has lighter green foliage, less upright habit, and longer stems than 'Cnem Pinka'.

'Cnem Pinka' was selected as one flowering plant within the progeny of the stated cross in January 2006 in a controlled environment in Andijk, Netherlands. The pollination took place in June 2005 and the seed sowing in October 2005.

The first act of asexual reproduction of 'Cnem Pinka' was accomplished using vegetative cuttings propagated from the initial selection in January 2006 in a controlled environment in Andijk, Netherlands.

Horticultural examination of plants grown from cuttings of the plant initiated in January 2006 in Andijk, Netherlands, and continuing thereafter, has demonstrated that the combination of characteristics as herein disclosed for 'Cnem Pinka' are firmly fixed and are retained through successive generations of asexual reproduction.

'Cnem Pinka' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cnem Pinka' has not been made publicly available more than one year prior to the filing of this application.

DESCRIPTION OF THE DRAWINGS

The accompanying photographic drawing shows typical flower and foliage characteristics of 'Cnem Pinka' with colors being as true as possible with an illustration of this type. The photographic drawing shows 2 flowering potted plants of the new variety in a gallon pot, and a close-up of the flowers. Both of the photographs were taken in April 2008 in Gilroy, Calif. USA. Both were grown in Gilroy, Calif. USA and were approximately 4–5 months old.

DETAILED BOTANICAL DESCRIPTION

The measurements were taken on May 27, 2008 on plants that were growing in 12 cm plastic pots. Culture of these plants started around Feb. 1, 2008 in Hillscheid, Germany. The plants were nearly 4 months old.

Color Chart used: Royal Horticultural Society Colour Chart (R.H.S.) 2001

BRIEF SUMMARY OF INVENTION

The following observations, measurements, and comparisons describe plants grown outside in Hillscheid, Germany. The following traits have been repeatedly observed and are determined to be basic characteristics of the new variety. The combination of these characteristics distinguishes this *Nemesia* as a new and distinct variety.

TABLE 1

DIFFERENCES BETWEEN THE NEW VARIETY 'CNEM PINKA' AND SIMILAR VARIETIES

| | 'Cnem Pinka' | 'Nemhrpur' (U.S. Plant Pat. No. 16,516) |
|---|---|---|
| Flower color | Lighter purple/pink, RHS 75A to RHS 75B, and white, bi-color | Darker purple/pink, RHS 70B, uniform |
| Flower size | Larger | Smaller |
| Stem size | Shorter and thicker | Longer and thinner |
| | 'Cnem Pinka' | 'Nemhapin' (U.S. Plant Pat. No. 18,530) |
| Flower color | Lighter purple/pink, RHS 75A to RHS 75B, and white, bi-color | Somewhat deeper purple/pink, RHS 75A or between RHS 70C and RHS 75A, uniform |
| Nectary | (Light) yellow | Creme |
| Plant habit | Bushy, semi-trailing, somewhat longer branches | Bushy, semi-upright |

Plant:

*Form, growth and habit.*—Relatively compact, semi-spreading, mounded, and well branched plant.

*Plant height.*—9–15 cm.

*Plant height (inflorescence included).*—13–18 cm.

*Plant width.*—45–50 cm.

Foliage:

*Arrangement.*—Single, opposite, and sometimes appear to be sessile.

*Immature, leaf color, upper surface.*—Between RHS 143A and 143B.

*Lower surface.*—RHS 138B.

*Mature, leaf color, upper surface.*—From RHS 137C.

*Lower surface.*—Between RHS 138A and B.

*Length.*—3.8–4.5 cm.

*Width.*—1.4–1.8 cm.

*Shape.*—Subulate to narrowly deltoid.

*Base shape.*—Obtuse to narrowly divided.

*Apex shape.*—Acute.

*Margin.*—Weakly serrate.

*Texture.*—Glabrous.

*Color of veins, upper surface.*—Indistinct.

*Color of veins, lower surface.*—RHS 144B.

*Leaf venation pattern.*—Intermediate between pinnate and parallel, that is: most side veins, but not all, branch at the base and run parallel.

*Color of petioles.*—RHS 144B.

*Length of petioles.*—0.1–0.3 cm.

*Width of petioles.*—0.3 cm.

*Texture of petioles.*—Glabrous.

Stem:

*Color of stem.*—RHS 143B.

*Length of stem.*—13–18 cm.

*Diameter.*—0.25–0.3 cm.

*Length of internodes.*—2.5–4 cm.

*Texture.*—Glabrous with sparse hirsute.

Inflorescence:

*Type.*—Usually one, occasionally 2 or 3 inflorescences at the end of the stem; terminal (located at shoot end) raceme with flowers in an alternate, and sometimes appears in small whorls.

*Flowering time.*—From late spring through early fall, and into fall in sheltered places.

*Inflorescence length.*—Most often about 7–10 cm.

*Inflorescence width.*—About 2.5–3 cm.

*Number of flowers.*—15–18, of which 6–9 flowers are open at the same time.

*Quantity of inflorescences per plant.*—Approximately 100.

*Lastingness of individual blooms on the plant.*—About 6–7 days depending on temperatures.

*Fragrance.*—Slightly sweet.

*Color of peduncle.*—RHS 137D.

*Length of peduncle.*—8–18 cm.

*Width of peduncle.*—2 mm.

*Texture of peduncle.*—Sparse hair.

*Texture of pedicel.*—Dense, very short hair.

*Color of pedicel.*—RHS 143C with no anthocyanins.

*Length of pedicel.*—Up to 0.1 cm and sometimes a little longer.

*Diameter of pedicel.*—0.1 cm.

Corolla:

*Form.*—Single, zygomorphic, 5-lobed, 3 petals, fused at the base and forming the fan-shaped upper lip; 2 petals completely fused, forming the lower lip; spurred.

*Length of flower.*—1.7–1.9 cm.

*Width of flower.*—0.6–0.7 cm.

*Depth of flower.*—0.6–0.7 cm.

*Nectar guide.*—Two yellow stripes, closely parallel on the top of upper lip, and leading/running into the throat, color RHS 5A, length 0.4–0.5 cm.

*Throat diameter.*—0.6 cm.

*Throat diameter at base of flower.*—0.2–0.3 cm.

*Throat color.*—Very pale pink, RHS 69D for the upper part; yellow, RHS 8B for the lower part (lower lip).

*Funnel length.*—0.5–0.6 cm.

*Funnel color.*—RHS 69D.

*Color upper lip, upper surface.*—RHS 75A to RHS 75B.

*Color upper lip, lower surface.*—RHS 76C to D.

*Color lower lip, upper surface.*—About RHS 69D or almost white; with a basal blotch of RHS 5A.

*Color lower lip, lower surface.*—RHS N155B.

*Length of upper lip.*—1.2–1.3 cm.

*Width of upper lip.*—0.8–0.9 cm.

*Length of lower lip.*—0.9–1.0 cm.

*Width of lower lip.*—0.8–0.9 cm.

*Shape of upper petals.*—Obovate.

*Apex.*—Rounded, the middle petal not slightly, but deeply divided.

*Base shape.*—Fused.

*Petal margin.*—Entire.

*Shape of lower petals.*—Completely fused and moulded.

*Apex.*—Weakly rounded, wavy.

*Base.*—Fused.

*Margin.*—Entire, apart from one or two notches at the apex.

*Petal texture (upper and lower surfaces).*—Papillose.

*Color of spur.*—RHS 11B to C, and RHS 11D at the tip.

*Length of spur.*—0.5 cm.

*Width of spur.*—From 1 mm at tip to 2 mm at base.

Bud (just before opening):

*Color.*—RHS 155A to very pale RHS 69D.

*Length of bud.*—0.6–0.7 cm.

*Width of bud.*—0.3 cm.

*Shape.*—Initially roughly ovate, then flattens to 'oyster-shape' just before unfolding.

*Number of sepals.*—5.

*Color of sepals (upper and lower surfaces).*—RHS 143C with no anthocyanins.

*Length of sepals.*—0.25 cm.
*Width of sepals.*—0.15 cm.
*Sepal shape.*—Lanceolate to narrowly elliptical.
*Apex shape.*—Acute.
*Margins.*—Entire.
*Texture of sepals* (*outward surface*).—Dense fine pubescent; glandular hairs.
*Texture of sepals* (*inner surface*).—Nearly glabrous.

Reproductive organs:
*Pistil.*—One.
*Length.*—0.3–0.4 cm.
*Style color.*—RHS 157D.
*Style length.*—0.1–0.2 cm.
*Stigma color.*—RHS 157A.
*Ovary.*—One, oval.
*Ovary color.*—RHS 143C.
*Number of stamen.*—4; 2 pairs with anthers coherent that are somewhat twisting around the pistil.
*Color of filaments.*—RHS 155A.
*Length of filaments.*—One pair 0.3–0.4 cm and another pair 0.2–0.3 cm.
*Anther shape.*—Ovate.
*Anther diameter.*—1 mm.
*Anther color.*—RHS 13D.
*Pollen quantity.*—Moderate.
*Color of pollen.*—RHS 8A.
*Fertility/seed set.*—Not observed on this hybrid.

Disease/pest resistance: Disease resistance or susceptibility has not been observed on this hybrid.

What is claimed is:

1. A new and distinct variety of *Nemesia* plant named 'Cnem Pinka', substantially as illustrated and described herein.

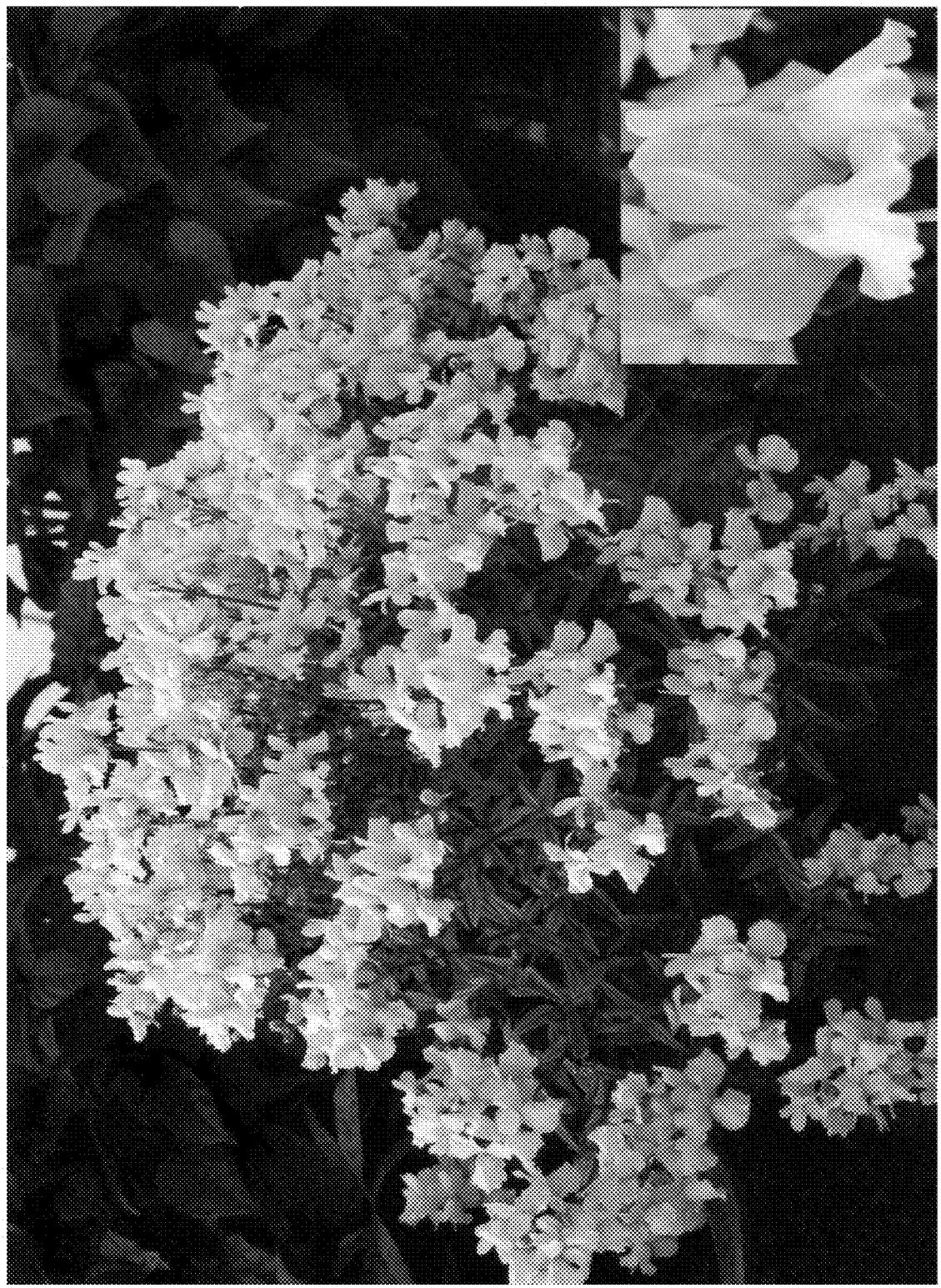

* * * * *